United States Patent
Bathe et al.

(10) Patent No.: US 6,734,002 B2
(45) Date of Patent: May 11, 2004

(54) NUCLEOTIDE SEQUENCES CODING FOR THE CHRS PROTEIN

(75) Inventors: Brigitte Bathe, Salzkotten (DE); Natalie Schischka, Bielefeld (DE); Achim Marx, Bielefeld (DE); Walter Pfefferle, Halle (DE)

(73) Assignee: Degussa AG, Duesseldorf (DE)

( * ) Notice: Subject to any disclaimer, the term of this patent is extended or adjusted under 35 U.S.C. 154(b) by 89 days.

(21) Appl. No.: 09/948,774

(22) Filed: Sep. 10, 2001

(65) Prior Publication Data

US 2002/0055114 A1 May 9, 2002

(30) Foreign Application Priority Data

Sep. 9, 2000 (DE) .......................... 100 44 753
Feb. 24, 2001 (DE) .......................... 101 09 022

(51) Int. Cl.[7] ................................. C12N 9/12
(52) U.S. Cl. .................. 435/194; 435/183; 435/193; 435/52.3; 435/252.32; 435/320.1; 536/23.2
(58) Field of Search .................. 435/183, 193, 435/194, 252.3, 252.32, 320.1; 536/23.2

(56) References Cited

U.S. PATENT DOCUMENTS 6,071,894 A    6/2000   Wallis

FOREIGN PATENT DOCUMENTS

EP    1 108 790    6/2001

OTHER PUBLICATIONS

Attwood et al. Which craft is best in bioinformatics? Comput. Chem. 2001, vol. 25(4), pp. 329–339.*

Ponting, C.P. Issues in predicting protein function from sequence. Brief. Bioinform. Mar. 2001, vol. 2(1), pp. 19–29.*

Kraev. Accession AJ009861. Aug. 11, 1998 (Alignment No. 1).*

M. P. Schmitt, Journal of Bacteriology, vol. 181, No. 17, XP-002196910, pp. 5330–5340, "Identification of a Two–Component Signal Transduction System From Corynebacterium Diphtheriae That Activates Gene Expression in Response to the Presence of Heme and Hemoglobin", Sep. 1999.

* cited by examiner

*Primary Examiner*—Ponnathapuachuta Murthy
*Assistant Examiner*—Christian L Fronda
(74) *Attorney, Agent, or Firm*—Oblon, Spivak, McClelland, Maier & Neustadt, P.C.

(57) ABSTRACT

The invention provides nucleotide sequences from Coryneform bacteria coding for the ChrS protein and a process for the fermentative preparation of amino acids using bacteria in which the ChrS protein is attenuated.

26 Claims, 1 Drawing Sheet

Figure 1: Plasmid pCR2.1chrSint

SEQUENCE LISTING

<160> NUMBER OF SEQ ID NOS: 4

<210> SEQ ID NO 1
<211> LENGTH: 1840
<212> TYPE: DNA
<213> ORGANISM: Corynebacterium glutamicum
<220> FEATURE:
<221> NAME/KEY: CDS
<222> LOCATION: (302)..(1558)
<223> OTHER INFORMATION:

<400> SEQUENCE: 1

```
acttggatca atccgcttcg tattcggcga cagcattgtg gctgatatct tggcctacac      60
cccattcgcc gcgatcagtg accttgtcca aatcggctgg gctggcgcca ccttcgccga     120
cagcgttggt ggagtagagg cagcaaactt cgctggaatt ttccaagaca tgctcatacc     180
acttggaatt ctggcagcgt ggacagctgc agcggtgtgg gcggcgaacc gctacatgcg     240
ctgggactcg taccgctaag cctgcagccg acgggattaa ggcagctaac attgagacac     300 g atg aat aaa gat ttc tgg acc gca ggc tgg acc gcc cgc tgg ttt tcg     349
  Met Asn Lys Asp Phe Trp Thr Ala Gly Trp Thr Ala Arg Trp Phe Ser
  1               5                  10                  15 cgc ggg gtt tcc ctt ttg gcc agc cca gtt acc gcc cca ctg aac tct         397
Arg Gly Val Ser Leu Leu Ala Ser Pro Val Thr Ala Pro Leu Asn Ser
             20                  25                  30 tgg cgg aga ttg cct aac ttg gcc aag tac acc ctc tac acc agg gtg         445
Trp Arg Arg Leu Pro Asn Leu Ala Lys Tyr Thr Leu Tyr Thr Arg Val
         35                  40                  45 tcg ttg caa gcg atc ccc gtg gtg ttg ctg tcg gcg tat ttc ctg ggc         493
Ser Leu Gln Ala Ile Pro Val Val Leu Leu Ser Ala Tyr Phe Leu Gly
     50                  55                  60 atc gta gct aat gca ggc acc ctg aat ccc tca ttt gtg tgg ctg ctg         541
Ile Val Ala Asn Ala Gly Thr Leu Asn Pro Ser Phe Val Trp Leu Leu
 65                  70                  75                  80 ggt ttc tcg gtc atc ctt tta ata gtg acg gta ttg gtt tat gaa tat         589
Gly Phe Ser Val Ile Leu Leu Ile Val Thr Val Leu Val Tyr Glu Tyr
                 85                  90                  95 cag cca tcg ctg aat tct cat cct agg cgc agc gta cag ccg ttc ttc         637
Gln Pro Ser Leu Asn Ser His Pro Arg Arg Ser Val Gln Pro Phe Phe
            100                 105                 110 ttc acc ggg ttg gtg ctc aac gtt tta ggc gtt gtg gtg tct gtg gtg         685
Phe Thr Gly Leu Val Leu Asn Val Leu Gly Val Val Val Ser Val Val
        115                 120                 125 ctt caa att ccg ggc tta aac atg tcg gac aac acc cga gca act gcc         733
```

```
Leu Gln Ile Pro Gly Leu Asn Met Ser Asp Asn Thr Arg Ala Thr Ala
        130                 135                 140 ctt att ttc act ctt acc tgc gta ttt ctg ctt tcg atc gcc tac att      781
Leu Ile Phe Thr Leu Thr Cys Val Phe Leu Leu Ser Ile Ala Tyr Ile
145                 150                 155                 160 ccg tgg atg aat tac cga tgg gtt tgg ctg atc gca atg tct gca gtg      829
Pro Trp Met Asn Tyr Arg Trp Val Trp Leu Ile Ala Met Ser Ala Val
                165                 170                 175 ttg tgg tgg acc agc aca acg act gat tat tta agt gca ttg tgg gtg      877
Leu Trp Trp Thr Ser Thr Thr Thr Asp Tyr Leu Ser Ala Leu Trp Val
                180                 185                 190 gtt atc ccg cca ctc atg gca gga acc gtc cga ctt tcc gta tgg acc      925
Val Ile Pro Pro Leu Met Ala Gly Thr Val Arg Leu Ser Val Trp Thr
            195                 200                 205 gtc gat gtc atg aaa gag gtt gag cgt tcc cgc gaa ttg gaa gcc tcc      973
Val Asp Val Met Lys Glu Val Glu Arg Ser Arg Glu Leu Glu Ala Ser
        210                 215                 220 ctc cgc gtc acc gaa gaa cgc ctt cgt ttc gcc cag gaa ctc cac gac     1021
Leu Arg Val Thr Glu Glu Arg Leu Arg Phe Ala Gln Glu Leu His Asp
225                 230                 235                 240 act tta gga caa cac ctg gcg gca atg tcc gtg aaa tca gaa ctg gcg     1069
Thr Leu Gly Gln His Leu Ala Ala Met Ser Val Lys Ser Glu Leu Ala
                245                 250                 255 ctt gcc ctg gcg aaa cgc ggc gac gac cgc ctc gaa aac gag ctg cgt     1117
Leu Ala Leu Ala Lys Arg Gly Asp Asp Arg Leu Glu Asn Glu Leu Arg
                260                 265                 270 gag ctc caa aaa ctc acc cgc acc tcc atg tcg gaa atg cgc gac gtc     1165
Glu Leu Gln Lys Leu Thr Arg Thr Ser Met Ser Glu Met Arg Asp Val
            275                 280                 285 gtc tcc ggc tac cgc acc gtc aac ctc gcc acg gaa atc gag ggc gct     1213
Val Ser Gly Tyr Arg Thr Val Asn Leu Ala Thr Glu Ile Glu Gly Ala
        290                 295                 300 aaa agt ttg ctt gcc gac gcc cac atc cac ctt tcc gtc atc ggc acc     1261
Lys Ser Leu Leu Ala Asp Ala His Ile His Leu Ser Val Ile Gly Thr
305                 310                 315                 320 acg tcc cag gtg tca ccc gct cac cga gaa ctg tgc gcg tgg ctt gtc     1309
Thr Ser Gln Val Ser Pro Ala His Arg Glu Leu Cys Ala Trp Leu Val
                325                 330                 335 cgg gaa gcc acc aca aac att ctg cgc cac tct gat gca acg gat gcc     1357
Arg Glu Ala Thr Thr Asn Ile Leu Arg His Ser Asp Ala Thr Asp Ala
                340                 345                 350 acc ctc acg ttg agc agc aca gag gtg cgc atg gac aac aat ggt gtg     1405
Thr Leu Thr Leu Ser Ser Thr Glu Val Arg Met Asp Asn Asn Gly Val
            355                 360                 365 aac aag gac atc ggc aga ctc tct ggt ctc agc gcc ctg cgc tca cga     1453
Asn Lys Asp Ile Gly Arg Leu Ser Gly Leu Ser Ala Leu Arg Ser Arg
        370                 375                 380 gcg gaa tca gcc gga atg acg ctc att gtg tcc cgc gaa gac gac cag     1501
Ala Glu Ser Ala Gly Met Thr Leu Ile Val Ser Arg Glu Asp Asp Gln
385                 390                 395                 400 ttc agc gtc cgc atg ctc att aat gca cct gca aat aca cct gca gaa     1549
Phe Ser Val Arg Met Leu Ile Asn Ala Pro Ala Asn Thr Pro Ala Glu
                405                 410                 415 aag gaa gct taaatgattt ccatttccat cgccgacgac gaagccctga            1598
Lys Glu Ala tcgcaagctc cctggcaacc ttgctcagct tggaacccga tttagacgtc cgacctaccg  1658
caggatccgg tgaagaactc attgaaacgt gggcggatcc aagcaaccga accgatgtat  1718
gcgtccttga ccttcaactc ggaggcatcg acggcatcga caccgccacc cggctcatgg  1778
```

```
aaaccacccc agatttggcc gtgctcatcg tgaccagcca cgccaggccc cgacaactca    1838
aa                                                                   1840
```

<210> SEQ ID NO 2
<211> LENGTH: 419
<212> TYPE: PRT
<213> ORGANISM: Corynebacterium glutamicum

<400> SEQUENCE: 2

```
Met Asn Lys Asp Phe Trp Thr Ala Gly Trp Thr Ala Arg Trp Phe Ser
1               5                   10                  15

Arg Gly Val Ser Leu Leu Ala Ser Pro Val Thr Ala Pro Leu Asn Ser
            20                  25                  30

Trp Arg Arg Leu Pro Asn Leu Ala Lys Tyr Thr Leu Tyr Thr Arg Val
        35                  40                  45

Ser Leu Gln Ala Ile Pro Val Leu Leu Ser Ala Tyr Phe Leu Gly
    50                  55                  60

Ile Val Ala Asn Ala Gly Thr Leu Asn Pro Ser Phe Val Trp Leu Leu
65                  70                  75                  80

Gly Phe Ser Val Ile Leu Leu Ile Val Thr Val Leu Val Tyr Glu Tyr
                85                  90                  95

Gln Pro Ser Leu Asn Ser His Pro Arg Arg Ser Val Gln Pro Phe Phe
            100                 105                 110

Phe Thr Gly Leu Val Leu Asn Val Leu Gly Val Val Ser Val Val
            115                 120                 125

Leu Gln Ile Pro Gly Leu Asn Met Ser Asp Asn Thr Arg Ala Thr Ala
130                 135                 140

Leu Ile Phe Thr Leu Thr Cys Val Phe Leu Leu Ser Ile Ala Tyr Ile
145                 150                 155                 160

Pro Trp Met Asn Tyr Arg Trp Val Trp Leu Ile Ala Met Ser Ala Val
                165                 170                 175

Leu Trp Trp Thr Ser Thr Thr Thr Asp Tyr Leu Ser Ala Leu Trp Val
            180                 185                 190

Val Ile Pro Pro Leu Met Ala Gly Thr Val Arg Leu Ser Val Trp Thr
        195                 200                 205

Val Asp Val Met Lys Glu Val Glu Arg Ser Arg Glu Leu Glu Ala Ser
210                 215                 220

Leu Arg Val Thr Glu Glu Arg Leu Arg Phe Ala Gln Glu Leu His Asp
225                 230                 235                 240

Thr Leu Gly Gln His Leu Ala Ala Met Ser Val Lys Ser Glu Leu Ala
                245                 250                 255

Leu Ala Leu Ala Lys Arg Gly Asp Asp Arg Leu Glu Asn Glu Leu Arg
            260                 265                 270

Glu Leu Gln Lys Leu Thr Arg Thr Ser Met Ser Glu Met Arg Asp Val
        275                 280                 285

Val Ser Gly Tyr Arg Thr Val Asn Leu Ala Thr Glu Ile Glu Gly Ala
    290                 295                 300

Lys Ser Leu Leu Ala Asp Ala His Ile His Leu Ser Val Ile Gly Thr
305                 310                 315                 320

Thr Ser Gln Val Ser Pro Ala His Arg Glu Leu Cys Ala Trp Leu Val
                325                 330                 335

Arg Glu Ala Thr Thr Asn Ile Leu Arg His Ser Asp Ala Thr Asp Ala
            340                 345                 350
```

-continued

```
Thr Leu Thr Leu Ser Ser Thr Glu Val Arg Met Asp Asn Asn Gly Val
        355                 360                 365

Asn Lys Asp Ile Gly Arg Leu Ser Gly Leu Ser Ala Leu Arg Ser Arg
    370                 375                 380

Ala Glu Ser Ala Gly Met Thr Leu Ile Val Ser Arg Glu Asp Asp Gln
385                 390                 395                 400

Phe Ser Val Arg Met Leu Ile Asn Ala Pro Ala Asn Thr Pro Ala Glu
                405                 410                 415

Lys Glu Ala

<210> SEQ ID NO 3
<211> LENGTH: 19
<212> TYPE: DNA
<213> ORGANISM: Corynebacterium glutamicum

<400> SEQUENCE: 3
catcgctgaa ttctcatcc                                              19

<210> SEQ ID NO 4
<211> LENGTH: 19
<212> TYPE: DNA
<213> ORGANISM: Corynebacterium glutamicum

<400> SEQUENCE: 4
ctgatttcac ggacattgc                                              19
```

NUCLEOTIDE SEQUENCES CODING FOR THE CHRS PROTEIN

CROSS-REFERENCE TO RELATED APPLICATIONS

The present application claims priority to German Application No. DE 100 44 7563.8, which was filed on Sep. 9, 2000 and German Application No. DE 101 09 022.6, which was filed on Feb. 24, 2001; the entire contents of both documents are incorporated herein by reference.

BACKGROUND OF THE INVENTION

1. Field of the Invention

The invention provides nucleotide sequences from Coryneform bacteria coding for the ChrS protein and a process for the fermentative preparation of amino acids using bacteria in which the ChrS protein is attenuated.

2. Discussion of the Background

L-amino acids, in particular lysine, are used in human medicine and in the pharmaceutical industry, in the foodstuffs industry and very particularly in animal nutrition.

It is known that amino acids can be prepared by the fermentation of strains of Coryneform bacteria, in particular *Corynebacterium glutamicum*. Due to the great importance of this area, constant efforts are made to improve the methods of preparing amino acids. Process improvements may relate to fermentation technology such as stirring and supplying with oxygen, altering the composition of the nutrient media such as the sugar concentration during fermentation, working up to the product by, for example, ion exchange chromatography, or the altering the intrinsic performance of the microorganims.

To improve the performance properties of these microorganisms, methods of mutagenesis, selection and mutant choice are often applied. These methods yield strains that are resistant to antimetabolites or are auxotrophic for regulatory significant metabolites and which produce amino acids.

Methods of recombinant DNA engineering have also been used for Corynebacterium strains to improve L-amino acid production. Such methods involve amplifying individual amino acid biosynthesis genes and examining the effects on amino acid production.

However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that attenuation of the chrs gene encoding the ChrS histidine kinase would improve L-amino acid yields.

SUMMARY OF THE INVENTION

An object of the present invention is to provide novel measures for the improved production of L-amino acids or amino acid, where these amino acids include L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan, L-arginine and the salts (monohydrochloride or sulfate) thereof.

One object of the present invention is providing a novel process for improving the fermentative production of said L-amino acids, particularly L-lysine. Such a process includes enhanced bacteria, preferably enhanced Coryneform bacteria, which express attenuated amounts of a ChrS hisitine kinase or protein that has ChrS histidine kinase activity.

Thus, another object of the present invention is providing such a bacterium, which expresses an attenuated amount of a ChrS protein or gene products of the chrS gene.

Another object of the present invention is providing a bacterium, preferably a Coryneform bacterium, which expresses a polypeptide that has an attenuated ChrS histidine kinase activity.

Another object of the invention is to provide a nucleotide sequence encoding a polypeptide having the ChrS protein sequence. One embodiment of such a sequence is the nucleotide sequence of SEQ ID NO: 1.

A further object of the invention is a method of making ChrS protein or an isolated polypeptide having a ChrS histidine kinase activity, as well as use of such isolated polypeptides in the production of amino acids. One embodiment of such a polypeptide is the polypeptide having the amino acid sequence of SEQ ID NO: 2.

Other objects of the invention include methods of detecting nucleic acid sequences homologous to SEQ ID NO: 1, particularly nucleic acid sequences encoding polypeptides that have ChrS histidine kinase activity, and methods of making nucleic acids encoding such polypeptides.

The above objects highlight certain aspects of the invention. Additional objects, aspects and embodiments of the invention are found in the following detailed description of the invention.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Cold Spring Harbor Laboratory, New York (1989), Current Protocols in Molecular Biology, Ausebel et al (eds), John Wiley and Sons, Inc. New York (2000)and the various references cited therein.

"L-amino acids" or "amino acids" as used herein mean one or more amino acids, including their salts, chosen from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophane and L-arginine. Lysine is particularly preferred.

When L-lysine or lysine is mentioned in the following, this is intended to mean not only the bases but also salts such as e.g. lysine monohydrochloride or lysine sulfate.

The invention provides a polynucleotide isolated from Coryneform bacteria and containing a polynucleotide sequence coding for the chrS gene, chosen from the group consisting of a) a polynucleotide which is at least 70% identical to a polynucleotide which codes for a polypeptide which contains the amino acid sequence in SEQ ID No. 2, b) a polynucleotide which codes for a polypeptide which contains an amino acid sequence which is at least 70% identical to the amino acid sequence in SEQ ID No. 2, c) a polynucleotide which is complementary to the polynucleotides in a) or b), and d) a polynucleotide containing a sequence of at least 15 consecutive nucleotides from the polynucleotide sequence in a), b) or c), wherein the polypeptide preferably has the activity of the sensor histidine kinase ChrS.

The invention also provides the polynucleotide mentioned above, wherein it is preferably a replicable DNA containing:

(i) the nucleotide sequence given in SEQ ID No.1, or (ii) at least one sequence which corresponds to sequence (i) within the range of degeneracy of the genetic code, or (iii) at least one sequence which hybridizes with sequences which are complementary to sequences (i) or (ii), and optionally (iv) functionally neutral sense mutations in (i).

The invention also provides:

a replicable polynucleotide, in particular DNA, containing the nucleotide sequence shown in SEQ ID No.1;

a polynucleotide which codes for a polypeptide which contains the amino acid sequence shown in SEQ ID No. 2;

a vector containing part of the polynucleotide according to the invention, but at least 15 consecutive nucleotides from the claimed sequence, and Coryneform bacteria in which the chrS gene is attenuated, in particular by an insertion or a deletion.

The invention also provides polynucleotides which consist substantially of a polynucleotide sequence which are obtainable by the screening, by means of hybridization, of a suitable gene library from a Coryneform bacterium which contains the complete gene or a part thereof, with a probe which contains the sequence in the polynucleotide according to the invention in accordance with SEQ ID No.1 or a fragment thereof and isolating the polynucleotide sequence mentioned.

Polynucleotides which contain sequences in accordance with the invention are suitable as hybridization probes for RNA, cDNA and DNA, in order to isolate nucleic acids or polynucleotides or genes of full length which code for the sensor histidine kinase ChrS, or in order to isolate nucleic acids, polynucleotides or genes which exhibit a high similarity to the sequence in the chrS gene. They are also suitable for incorporation into so-called arrays, micro-arrays or DNA chips in order to detect and determine the corresponding polynucleotides.

Furthermore, polynucleotides which contain the sequence in accordance with the invention are also suitable as primers, with the aid of which, and using the polymerase chain reaction (PCR), the DNA of genes which code for the sensor histidine kinase ChrS can be prepared.

Those oligonucleotides which are used as probes or primers contain at least 25, 26, 27, 28, 29 or 30, preferably at least 20, 21, 22, 23 or 24, very particularly preferably at least 15, 16, 17, 18 or 19 consecutive nucleotides. Oligonucleotides with a length of at least 31, 32, 33, 34, 35, 36, 37, 38, 39 or 40, or at least 41, 42, 43, 44, 45, 46, 47, 48, 49 or 50 nucleotides are also suitable. optionally, oligonucleotides with a length of at least 100, 150, 200, 250 or 300 nucleotides are also suitable.

"Isolated" means separated from its natural surroundings.

A "polynucleotide" generally refers to polyribonucleotides and polydeoxyribonucleotides, wherein these may be non-modified RNA or DNA or modified RNA or DNA.

Polynucleotides according to the invention include a polynucleotide in accordance with SEQ ID No. 1 or a fragment prepared therefrom and also those which are at least 70% to 80%, preferably at least 81% to 85%, particularly preferably at least 86% to 90%, and very particularly preferably at least 91%, 93%, 95%, 97% or 99% identical to the polynucleotide in accordance with SEQ ID No. 1 or a fragment prepared therefrom.

"Polypeptides" are understood to be peptides or proteins which contain two or more amino acids linked via peptide bonds.

Polypeptides according to the invention include a polypeptide in accordance with SEQ ID No. 2, in particular those with the biological activity of the sensor histidine kinase ChrS and also those which are at least 70% to 80%, preferably at least 81% to 85%, particularly preferably at least 86% to 90%, and very particularly preferably at least 91%, 93%, 95%, 97% or 99% identical to the polypeptide in accordance with SEQ ID No. 2 and have the activity mentioned above.

Furthermore, the invention provides a process for the fermentative preparation of amino acids chosen from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophane and L-arginine, using Coryneform bacteria, in particular those which already produce amino acids and in which the nucleotide sequences coding for the chrS gene are attenuated, in particular switched off or expressed at a low level.

In this context, the expression "attenuation" describes the reduction or switching off of the intracellular activity of one or more enzymes (proteins) in a microorganism which are coded by the corresponding DNA, for example by using a weak promoter or by using a gene or allele which codes for a corresponding enzyme with a low activity or inactivates the corresponding gene or enzyme (protein) and optionally combining these measures.

As a result of the attenuation measures, the activity or concentration of the corresponding protein is generally lowered to 0 to 75%, 0 to 50%, 0 to 25%, 0 to 10% or 0 to 5% of the activity or concentration of the wild type protein, or of the activity or concentration of the protein in the initially used microorganism.

Microorganisms which are provided by the present invention can produce amino acids from glucose, saccharose, lactose, fructose, maltose, molasses, starch, cellulose or from glycerine and ethanol. They are representatives of Coryneform bacteria, in particular of the genus Corynebacterium. From among the genus Corynebacterium, the species *Corynebacterium glutamicum* has to be mentioned in particular, this being recognized by a person skilled in the art for its ability to produce L-amino acids.

Suitable strains of the genus Corynebacterium, in particular of the species *Corynebacterium glutamicum* (*C. glutamicum*), are in particular the known wild type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020
and L-amino acid-producing mutants or strains prepared therefrom.

Preferably, a bacterial strain with attenuated expression of a chrS gene that encodes a polypeptide with ChrS histidine kinase activity will improve amino acid yield at least 1%.

The new chrS gene coding for the sensor histidine kinase ChrS was isolated from *C. glutamicum*. The sensor histidine kinase ChrS is part of a two-component system. Two component regulation systems are characterized in that different response-regulator proteins can be activated by sensor kinases.

In order to isolate the chrS gene, or also other genes, from *C. glutamicum*, a gene library from this microorganism is first compiled in *Escherichia coli* (*E. coli*). The compilation of gene libraries is described in generally known textbooks and manuals. The text book by Winnacker: Gene und Klone, Eine Einführung in die Gentechnologie (Verlag Chemie, Weinheim, Germany, 1990), or the manual by Sambrook et al.: Molecular Cloning, A Laboratory Manual (Cold Spring Harbor Laboratory Press, 1989) may be mentioned as examples. A very well-known gene library is that of the *E. coli* K-12 strain W3110, which was compiled by Kohara et al. (Cell 50, 495–508 (1987)) in λ-vectors. Bathe et al. (Molecular and General Genetics, 252:255–265, 1996) describe a gene library from *C. glutamicum* ATCC13032, which was compiled with the aid of the cosmid vector SuperCos I (Wahl et al., 1987, Proceedings of the National Academy of Sciences USA, 84:2160–2164) in *E. coli* K-12 strain NM554 (Raleigh et al., 1988, Nucleic Acids Research 16:1563–1575).

Again, Börmann et al. (Molecular Microbiology 6(3), 317–326 (1992)) describe a gene library from *C. glutamicum* ATCC13032 obtained using the cosmid pHC79 (Hohn and Collins, 1980, Gene 11, 291–298).

To prepare a gene library from *C. glutamicum* in *E. coli*, plasmids such as pBR322 (Bolivar, 1979, Life Sciences, 25, 807–818) or pUC9 (Vieira et al., 1982, Gene, 19:259–268) may also be used. Particularly suitable hosts are those *E. coli* strains which are restriction and recombination defective such as, for example, the strain DH5αmcr which was described by Grant et al. (Proceedings of the National Academy of Sciences USA, 87 (1990) 4645–4649). The long DNA fragments cloned with the aid of cosmids or other vectors are then again subcloned in suitable vectors commonly used for DNA sequencing and then sequenced, as is described e.g. in Sanger et al. (Proceedings of the National Academy of Sciences of the United States of America, 74:5463–5467, 1977).

The DNA sequences obtained may then be examined using known algorithms or sequence analysis programs such as e.g. the one from Staden (Nucleic Acids Research 14, 217–232 (1986)), the one from Marck (Nucleic Acids Research 16, 1829–1836 (1988)) or the GCG program from Butler (Methods of Biochemical Analysis 39, 74–97 (1998)).

Additionally, methods employing DNA chips, microarrays or similar recombinant DNA technology that enables high throughput screening of DNA and polynucleotides which encode the ChrS histidine kinase or polynucleotides with homology to the chrS gene as described herein. Such methods are known in the art and are described, for example, in Current Protocols in Molecular Biology, Ausebel et al (eds), John Wiley and Sons, Inc. New York (2000).

The new DNA sequence from *C. glutamicum*, coding for the chrS gene, was found and, as SEQ ID No. 1, is a constituent of the present invention. Furthermore, the amino acid sequence for the corresponding protein was derived from the available DNA sequence using the methods described above. SEQ ID No. 2 gives the amino acid sequence in the chrS gene product which is obtained.

Coding DNA sequences which are produced from SEQ ID No. 1 by the degeneracy of the genetic code are also a constituent of the present invention. In the same way, DNA sequences which hybridize with SEQ ID No. 1 or parts of SEQ ID No. 1, are a constituent of the invention. Furthermore, in the specialist field, conservative amino acid replacements, such as e.g. replacing glycine by alanine or aspartic acid by glutamic acid, in proteins are known as sense mutations which do not lead to any fundamental change in the activity of the protein, i.e. they are functionally neutral. Furthermore, it is known that changes at the N-terminal and/or C-terminal of a protein does not substantially impair its function and may even stabilize it. A person skilled in the art may find information about this, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in well-known textbooks on genetics and molecular biology. Amino acid sequences which are produced from SEQ ID No. 2 in an appropriate manner are also a constituent of the invention.

In the same way, DNA sequences which hybridize with SEQ ID No. 1 or parts of SEQ ID No. 1 are a constituent of the invention. Finally, DNA sequences which are produced from SEQ ID No. 1 by the polymerase chain reaction (PCR) using primers are a constituent of the invention. These types of oligonucleotides typically have a length of at least 15 nucleotides.

Instructions for identifying DNA sequences by means of hybridization can be found by a person skilled in the art, inter alia, in the manual "The DIG System Users Guide for Filter Hybridization" from Boehringer Mannheim GmbH (Mannheim, Germany, 1993) and in Liebl et al. (International Journal of Systematic Bacteriology 41: 255–260 (1991)). Hybridization takes place under stringent conditions, which means that the only hybrids formed are those in which the probe and target sequence, i.e. the polynucleotides treated with the probes, are at least 70% identical. It is known that the stringency of hybridization, including the washing step, is affected or determined by varying the buffer composition, the temperature and the salt concentration. The hybridization reaction is preferably performed at relatively low stringency as compared with the washing step (Hybaid Hybridisation Guide, Hybaid Limited, Teddington, UK, 1996).

For the hybridization reaction, for example, a 5×SSC-buffer may be used at a temperature of about 50° C.–68° C. Probes may then also hybridize with polynucleotides which are less than 70% identical to the sequence in the probe. These hybrids are less stable and are removed by washing under stringent conditions. This may be achieved, for example, by lowering the salt concentration to 2×SSC and optionally then to 0.5×SSC (The DIG System User's Guide for Filter Hybridisation, Boehringer Mannheim, Mannheim, Germany, 1995), wherein a temperature of about 50° C.–68° C. is used. It is also optionally possible to lower the salt concentration to 0.1×SSC. By a stepwise increase in the hybridization temperature from 50° C. to 68° C., in steps of about 1–2° C., polynucleotide fragments can be isolated which are, for example, at least 70% or at least 80% or at least 90% to 95% identical to the sequence in the probe used. Further instructions for hybridization, in the form of so-called kits, are commercially available (e.g. DIG Easy Hyb from Roche Diagnostics GmbH, Mannheim, Germany, Catalogue No. 1603558).

A person skilled in the art may find instructions for the amplification of DNA sequences using the polymerase chain reaction (PCR), inter alia, in the manual by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

It was found that Coryneform bacteria produce amino acids in an improved manner following attenuation of the chrS gene.

To produce attenuation, either expression of the chrS gene or the regulatory or catalytic properties of the enzyme protein may be reduced or switched off. Optionally, both measures may be combined.

A reduction in gene expression may take place by appropriate culture management or by genetic modification (mutation) of the signal structures for gene expression. Signal structures for gene expression are, for example, repressor genes, activator genes, operators, promoters, attenuators, ribosome bonding sites, the start codon and terminators. A person skilled in the art may find information about these e.g. in patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Pátek et al. (Microbiology 142: 1297 (1996)), Vasicova et al. (Journal of Bacteriology 181: 6188 (1999)) and in well-known textbooks on genetics and molecular biology such as e.g. the textbook by Knippers ("Molekulare Genetik", 6th edition, Georg Thieme Verlag, Stuttgart, Germany, 1995) or the book by Winnacker ("Gene und Klone", VCH Verlagsgesellschaft, Weinheim, Germany, 1990).

Mutations which lead to a change or reduction in the catalytic properties of enzyme proteins are known from the prior art; the papers by Qiu and Goodman (Journal of Biological Chemistry 272: 8611–8617 (1997)), Sugimoto et al. (Bioscience Biotechnology and Biochemistry 61: 1760–1762 (1997)) and Möckel ("Die Threonindehydratase aus Corynebacterium glutamicum: Aufhebung der allosterischen Regulation und Struktur des Enzyms", Jülich Research Center, Reports, Jül-2906, ISSN09442952, Jülich, Germany, 1994) may be mentioned as examples. Reviews of the subject can be found in well-known textbooks on genetics and molecular biology such as e.g. the book by Hagemann ("Allgemeine Genetik", Gustav Fischer Verlag, Stuttgart, 1986).

Suitable mutations are transitions, transversions, insertions and deletions. Depending on the effect of amino acid replacement on the enzyme activity, reference is made to missense mutations or nonsense mutations. Insertions or deletions of at least one base pair (bp) in a gene lead to frame shift mutations, as a result of which incorrect amino acids are incorporated or translation is terminated prematurely. Deletions of several codons lead typically to complete failure of enzyme activity. Instructions for producing these types of mutations are part of the prior art and can be found in well-known textbooks on genetics and molecular biology such as e.g. the textbook by Knippers ("Molekulare Genetik", 6th edition, Georg Thieme Verlag, Stuttgart, Germany, 1995), the book by Winnacker ("Gene und Klone", VCH Verlagsgesellschaft, Weinheim, Germany, 1990) or the book by Hagemann ("Allgemeine Genetik", Gustav Fischer Verlag, Stuttgart, 1986).

A common method of mutating genes in C. glutamicum is the method of gene disruption and gene replacement described by Schwarzer and Pühler (Bio/Technology 9, 84–87 (1991)).

With the method of gene disruption a central part of the coding region of the gene being considered is cloned in a plasmid vector which can replicate in a host (typically E. coli), but not in C. glutamicum. Suitable vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Netherlands; Bernard et al., Journal of Molecular Biology, 234: 534–541 (1993)) or pEM1 (Schrumpf et al, 1991, Journal of Bacteriology 173:4510–4516). The plasmid vector which contains the central part of the coding region of the gene is then transferred by conjugation or transformation into the desired strain of C. glutamicum. The method of conjugation is described, for example, in Schäfer et al. (Applied and Environmental Microbiology 60, 756–759 (1994)). Methods for transforming are described, for example, in Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross-over" event, the coding region of the gene involved is disrupted by the vector sequence and two incomplete alleles are obtained, in which the 3'- or the 5'-ends respectively are each missing. This method was used, for example, by Fitzpatrick et al. (Applied Microbiology and Biotechnology 42, 575–580 (1994)) to switch off the recA gene in C. glutamicum.

With the method of gene replacement, a mutation such as e.g. a deletion, insertion or base replacement is produced in-vitro in the gene being considered. The allele produced is again cloned in a vector which does not replicate in C. glutamicum and this is then transferred by transformation or conjugation into the desired host for C. glutamicum. After homologous recombination by means of a first, integration-causing "cross-over" event and an appropriate second, excision-causing "cross-over" event in the target gene or in the target sequence, incorporation of the mutation or the allele is achieved. This method was used, for example, by Peters-Wendisch et al.(Microbiology 144, 915–927 (1998)) to switch off the pyc gene in C. glutamicum by means of a deletion.

A deletion, insertion or base replacement can be incorporated in the chrS gene in this way.

In addition, it may be advantageous for the production of L-amino acids, in addition to attenuating the chrS gene in one or more enzymes on the relevant biosynthetic pathway, to enhance, in particular overexpress, glycolysis, anaploretic processes, the citric acid cycle, the pentose-phosphate cycle, amino acid export and optionally regulatory proteins.

The expression "enhancement" in this context describes the increase in intracellular activity of one or more enzymes (proteins) in a microorganism which are coded by the corresponding DNA, for example by increasing the copy number for the gene or genes, by using a strong promoter or by using a gene or allele which codes for a corresponding enzyme (protein) with a high activity and optionally by combining these methods.

Due to the measures for enhancement, in particular overexpression, the activity or concentration of the corresponding protein is generally increased by at least 10%, 25%, 50%, 75%, 100%, 150%, 200%, 300%, 400% or 500%, with a maximum of up to 1000% or 2000%, with reference to the wild type protein or the activity or concentration of the protein in the initially used microorganism.

Thus, to prepare L-amino acids, apart from attenuating the chrS gene, one or more of the genes chosen from the group consisting of the dapA gene coding for dihydrodipicolinate synthase (EP-B 0 197 335), the gap gene coding for glyceraldehyde-3-phosphate dehydrogenase (Eikmanns (1992), Journal of Bacteriology 174:6076–6086), the tpi gene coding for triosephosphate isomerase (Eikmanns (1992), Journal of Bacteriology 174:6076–6086), the pgk gene coding for 3-phosphoglycerate kinase (Eikmanns (1992), Journal of Bacteriology 174:6076–6086), the zwf gene coding for glucose-6-phosphate dehydrogenase (JP-A-09224661), the pyc gene coding for pyruvate carboxylase (DE-A-198 31 609), the mqo gene coding for malate quinone oxidoreduktase (Molenaar et al., European Journal of Biochemistry 254, 395–403 (1998)), the lysC gene coding for a feed-back resistant aspartate kinase (EP-B-0387527; EP-A-0699759; WO 00/63388), the lysE gene coding for lysine export (DE-A-195 48 222), the hom gene coding for homoserine dehydrogenase (EP-A 0131171), the ilvA gene coding for threonine dehydratase (Mockel et al., Journal of Bacteriology (1992) 8065–8072)) or the ilvA (Fbr) allele coding for a "feed back resistant" threonine dehydratase (Mockel et al., (1994) Molecular Microbiology 13: 833–842), the ilvBN gene coding for acetohydroxyacid synthase (EP-B 0356739), the ilvD gene coding for dihydroxyacid dehydratase (Sahm and Eggeling (1999) Applied and Environmental Microbiology 65: 1973–1979), the zwa1 gene coding for Zwa1 protein (DE: 19959328.0, DSM 13115)

may be simultaneously enhanced, in particular overexpressed.

It may also be advantageous for the production of amino acids, apart from attenuating the chrS gene, to simultaneously attenuate, in particular to reduce the expression of, one or more genes chosen from the group the pck gene coding for phosphoenolpyruvate carboxykinase (DE 199 50 409.1, DSM 13047), the pgi gene coding for glucose-6-phosphate isomerase (U.S. Ser. No. 09/396,478, DSM 12969), the poxB gene coding for pyruvate oxidase (DE:1995 1975.7, DSM 13114)

the zwa2 gene coding for Zwa2 protein (DE: 19959327.2, DSM 13113).

Furthermore, it may be advantageous for the production of amino acids, apart from attenuating the chrS gene, to switch off undesired side reactions (Nakayama: "Breeding of Amino Acid Producing Microorganisms", in: Overproduction of Microbial Products, Krumphanzl, Sikyta, Vanek (eds.), Academic Press, London, UK, 1982).

Microorganisms prepared according to the invention are also provided by the invention and may be cultivated continuously or batchwise in a batch process or in a fed batch process or repeated fed batch process for the purposes of producing L-amino acids. A review of known cultivation processes is given in the text book by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used has to comply in a suitable manner with the requirements of the particular strain. Descriptions of culture media for different microorganisms are given in the manual "Manual of Methods for General Bacteriology" by the American Society for Bacteriology (Washington D.C., USA, 1981).

Sources of carbon which may be used are sugars and carbohydrates such as e.g. glucose, saccharose, lactose, fructose, maltose, molasses, starch and cellulose, oils and fats such as, for example, soya oil, sunflower oil, peanut oil and coconut fat, fatty acids such as, for example, palmitic acid, stearic acid and linoleic acid, alcohols such as, for example, glycerin and ethanol and organic acids such as, for example, acetic acid. These substances may be used individually or as a mixture.

Sources of nitrogen which may be used are organic nitrogen-containing compounds such as peptones, yeast extract, meat extract, malt extract, maize steep liquor, soya bean meal and urea or inorganic compounds such as ammonium sulfate, ammonium chloride, ammonium phosphate, ammonium carbonate and ammonium nitrate. The sources of nitrogen may be used individually or as a mixture.

Sources of phosphorus which may be used are phosphoric acid, potassium dihydrogen phosphate or dipotassium hydrogen phosphate or the corresponding sodium-containing salts. The culture medium must also contain salts of metals such as, for example, magnesium sulfate or iron sulfate, which are required for growth. Finally, essential growth-promoting substances such as amino acids and vitamins may be used in addition to the substances mentioned above. Suitable precursors may be added to the culture medium in addition to these. The feedstuffs mentioned may be added to the culture in the form of a single batch or be fed in a suitable manner during cultivation.

To regulate the pH of the culture, basic compounds such as sodium hydroxide, potassium hydroxide, ammonia or ammoniacal liquor or acid compounds such as phosphoric acid or sulfuric acid are used in an appropriate manner. To control the production of foam, antifoaming agents such as, for example, polyglycol esters of fatty acid may be used. To maintain the stability of plasmids, suitable selectively acting substances such as, for example, antibiotics, may be added to the medium. In order to maintain aerobic conditions, oxygen or oxygen-containing gas mixtures such as, for example, air, are passed into the culture. The temperature of the culture is normally 20° C. to 45° C. and is preferably 25° C. to 40° C. The culture procedure is continued until a maximum has been produced in the desired product. This objective is normally achieved within 10 hours to 160 hours.

Methods for determining L-amino acids are known from the prior art. Analysis may be performed, for example, as described in Spackman et al. (Analytical Chemistry, 30, (1958), 1190) by anion exchange chromatography followed by ninhydrin derivation, or it may be performed by reversed phase HPLC as described in Lindroth et al. (Analytical Chemistry (1979) 51: 1167–1174).

The process according to the invention is used for the fermentative preparation of amino acids.

The following microorganism was deposited on 12.01.2001 as a pure culture at the German Collection of Microorganisms and Cell Cultures (DSMZ, Braunschweig, Germany) in accordance with the Budapest Treaty:

Escherichia coli Top10/pCR2.1chrSint as DSM 13982.

The present invention is explained in more detail in the following by using embodiment examples.

Isolation of plasmid DNA from Escherichia coli and all the techniques for restriction, Klenow treatment and alkaline phosphatase treatment were performed in the way described in Sambrook et al. (Molecular Cloning. A Laboratory Manual, 1989, Cold Spring Harbor Laboratory Press, Cold Spring Harbor, N.Y., USA). Methods for the transformation of Escherichia coli are also described in this manual.

The composition of commonly used culture media such as LB medium or TY medium may also be found in the manual by Sambrook et al.

EXAMPLE 1
Production of a Genomic Cosmid Gene Library from C. glutamicum ATCC 13032

Chromosomal DNA from C. glutamicum ATCC 13032 was isolated as described in Tauch et al., (1995, Plasmid 33:168–179), and partly cleaved with the restriction enzyme Sau3AI (Amersham Pharmacia, Freiburg, Germany, product description Sau3AI, Code no. 27-0913-02). The DNA fragments were dephosphorylated with shrimp alkaline phosphatase (Roche Molecular Biochemicals, Mannheim, Germany, product description SAP, Code no. 1758250). The DNA in the cosmid vector SuperCos1 (Wahl et al. (1987), Proceedings of the National Academy of Sciences, USA 84:2160–2164), purchased from the Stratagene Co. (La Jolla, USA, product description SuperCos1 Cosmid Vektor Kit, Code no. 251301) was cleaved with the restriction enzyme XbaI (Amersham Pharmacia, Freiburg, Germany, product description XbaI, Code no. 27-0948-02) and also dephosphorylated with shrimp alkaline phosphatase.

Then the cosmid DNA was cleaved with the restriction enzyme BamHI (Amersham Pharmacia, Freiburg, Germany, product description BamHI, Code no. 27-0868-04). The cosmid DNA treated in this way was mixed with the treated ATCC13032 DNA and the mixture was treated with T4 DNA ligase (Amersham Pharmacia, Freiburg, Germany, product description T4-DNA-Ligase, Code no.27-0870-04). The ligation mixture was then packed into phages with the aid of Gigapack II XL Packing Extracts (Stratagene, La Jolla, USA, product description Gigapack II XL Packing Extract, Code no. 200217).

To infect E. coli strain NM554 (Raleigh et al. 1988, Nucleic Acid Res. 16:1563–1575), the cells were taken up in 10 mM $MgSO_4$ and mixed with an aliquot of the phage suspension. Infection and titering of the cosmid library was performed as described in Sambrook et al. (1989, Molecular Cloning: A Laboratory Manual, Cold Spring Harbor), wherein the cells were plated out on LB agar (Lennox, 1955, Virology, 1:190)+100 µg/ml ampicillin. After incubation overnight at 37° C., recombinant individual clones were selected.

EXAMPLE 2
Isolating and Sequencing the chrS Gene

The cosmid DNA from an individual colony was isolated with the Qiaprep Spin Miniprep Kit (Product No. 27106, Qiagen, Hilden, Germany) in accordance with the manufacturer's information and partly cleaved with the restriction enzyme Sau3AI (Amersham Pharmacia, Freiburg, Germany, product description Sau3AI, Product No. 27-0913-02). The DNA fragments were dephosphorylated with shrimp alkaline phosphatase (Roche Molecular Biochemicals, Mannheim, Germany, product description SAP, Product No. 1758250). After gel electrophoretic separation, isolation of the cosmid fragments in the size range 1500 to 2000 bp was performed with QiaExII Gel Extraction Kit (Product No. 20021, Qiagen, Hilden, Germany).

The DNA in sequencing vector pZero-1 purchased from the Invitrogen Co. (Groningen, Netherlands, product description Zero Background Cloning Kit, Product No. K2500-01) was cleaved with the restriction enzyme BamHI (Amersham Pharmacia, Freiburg, Germany, product description BamHI, Product No. 27-0868-04). Ligation of the cosmid fragments in sequencing vector pZero-1 was performed as described in Sambrook et al. (1989, Molecular Cloning: A Laboratory Manual, Cold Spring Harbor), wherein the DNA mixture was incubated overnight with T4 ligase (Pharmacia Biotech, Freiburg, Germany). This ligation mixture was then electroporated in E. coli strain DH5 MCR (Grant, 1990, Proceedings of the National Academy of Sciences, U.S.A., 87:4645–4649) (Tauch et al. 1994, FEMS Microbiol Letters, 123:343–7) and plated out on LB agar (Lennox, 1955, Virology, 1:190) with 50 µg/ml zeocin.

The plasmid preparation of recombinant clones was performed with Biorobot 9600 (Product No. 900200, Qiagen, Hilden, Germany). Sequencing was performed using the dideoxy chain termination method according to Sanger et al. (1977, Proceedings of the National Academies of Sciences, U.S.A., 74:5463–5467) with modifications by Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. Gel electrophoretic separation and analysis of the sequencing reaction was performed in a "Rotiphorese NF Acrylamid/Bisacrylamid" Gel (29:1) (Product No. A124.1, Roth, Karlsruhe, Germany) using the "ABI Prism 377" sequencing instrument from PE Applied Biosystems (Weiterstadt, Germany).

The crude sequencing data obtained were then processed using the Staden software package (1986, Nucleic Acids Research, 14:217–231) Version 97-0. The individual sequences of the pZero1 derivatives were assembled to give a cohesive contig. Computer aided coding region analyses were drawn up with the program XNIP (Staden, 1986, Nucleic Acids Research, 14:217–231). Further analyses were performed using the "BLAST search programs" (Altschul et al., 1997, Nucleic Acids Research, 25:33893402) against the non-redundant database of the "National Center for Biotechnology Information" (NCBI, Bethesda, Md., USA).

The nucleotide sequence obtained is given in SEQ ID No. 1. Analysis of the nucleotide sequence produced an open reading frame of 1260 bp, which was called the chrS gene. The chrS gene coded for a polypeptide of 419 amino acids.

EXAMPLE 3
Preparing an Integration Vector for Integration Mutagenesis of the chrS Gene Chromosomal DNA was isolated from the strain ATCC 13032 using the method described by Eikmanns et al.

(Microbiology 140: 1817–1828 (1994)). Based on the sequence of the chrS gene for *C. glutamicum*, known from example 2, the following oligonucleotides were chosen for the polymerase chain reaction (see SEQ ID No. 3 and SEQ ID No. 4):

chrS-int1:
5'CAT CGC TGA ATT CTC ATC C 3'
chrS-int2:
5'CTG ATT TCA CGG ACA TTG C 3'

The primers shown were synthesized by MWG Biotech (Ebersberg, Germany) and the PCR reaction was performed using the standard PCR method described by Innis et al. (PCR protocols. A guide to methods and applications, 1990, Academic Press) using Taq polymerase from Boehringer Mannheim (Germany, product description Taq DNA Polymerase, Product No. 1 146 165). With the aid of the polymerase chain reaction, the primers facilitated amplification of a 468 bp sized internal fragment of the chrS gene. The product amplified in this way was electrophoretically tested in a 0.8% strength agarose gel.

The amplified DNA fragment was ligated with the TOPO TA cloning kit from the Invitrogen Corporation (Carlsbad, Calif., USA; catalogue number K4500-01) in vector pCR2.1-TOPO (Mead at al. (1991) Bio/Technology 9:657–663).

Figure 1:
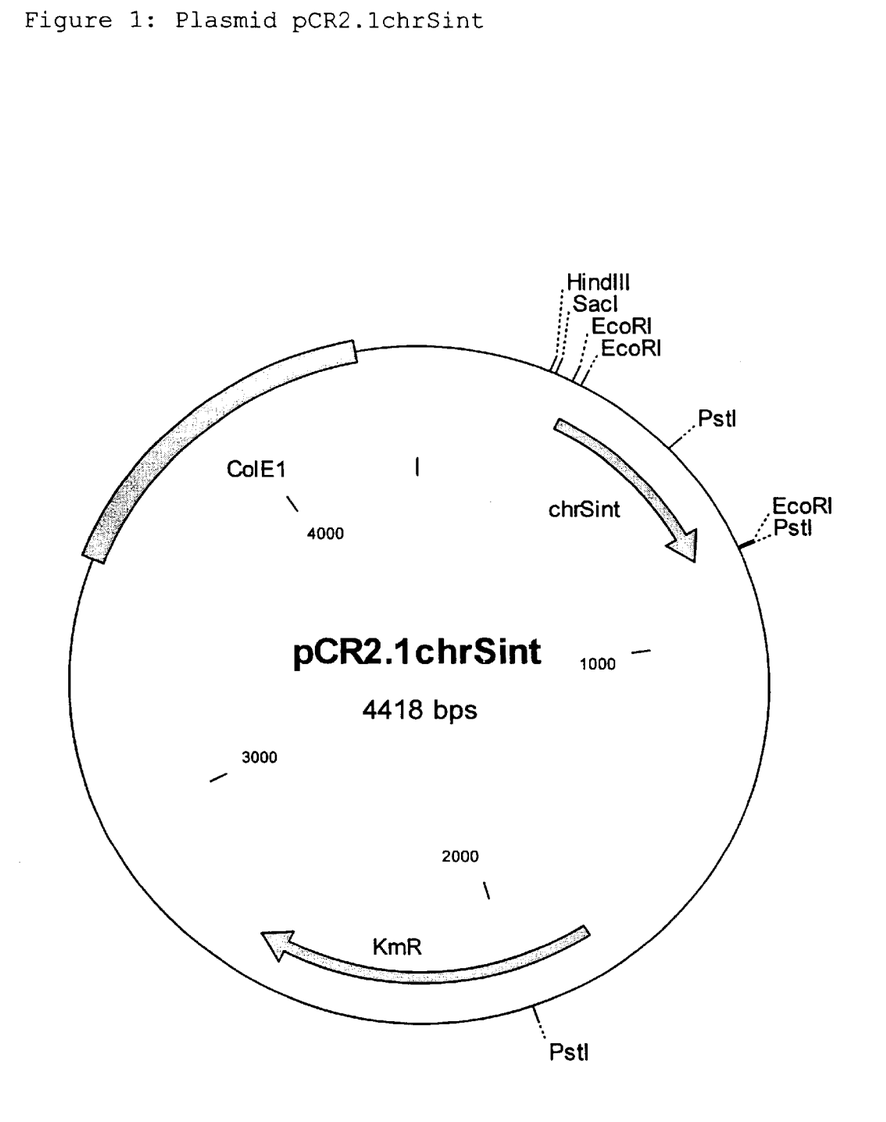
FIG. 1: Map of plasmid pCR2.1chrSint.

Then the *E. coli* strain TOP10 was electroporated with the ligation mixture (Hanahan, In: DNA cloning. A practical approach. Vol.I. IRL-Press, Oxford, Washington D.C., USA, 1985). The selection of plasmid-carrying cells was performed by plating out the transformation mixture on LB agar (Sambrook et al., Molecular cloning: a laboratory manual. $2^{nd}$ Ed. Cold Spring Harbor Laboratory Press, Cold Spring Harbor, N.Y., 1989) which had been supplemented with 50 mg/l kanamycin. Plasmid DNA was isolated from a transformant with the aid of the QIAprep Spin Miniprep kit from Qiagen and examined by restriction with the restriction enzyme EcoRI followed by agarose gel electrophoresis (0.8%). The plasmid was called pCR2.1chrSint and is shown in FIG. 1.

EXAMPLE 4
Integration Mutagenesis of the chrS Gene in the Strain DSM 5715

The vector called pCR2.1chrSint in example 3 was electroporated into *Corynebacterium glutamicum* DSM 5715 using the electroporation method described by Tauch et al.(FEMS Microbiological Letters, 123:343–347 (1994)). The strain DSM 5715 is an AEC resistant lysine producer. The vector pCR2.1chrSint cannot replicate itself in DSM5715 and only remains in the cells when it has been integrated into the chromosome of DSM 5715. The selection of clones with pCR2.1chrSint integrated into the chromosome was performed by plating out the electroporation mixture on LB agar (Sambrook et al., Molecular cloning: a laboratory manual. $2^{nd}$ Ed. Cold Spring Harbor Laboratory Press, Cold Spring Harbor, N.Y.) which had been supplemented with 15 mg/l kanamycin.

To prove that integration has occurred, the chrSint fragment is labeled with the Dig hybridization kit from Boehringer using the method described in "The DIG System Users Guide for Filter Hybridization" from Boehringer Mannheim GmbH (Mannheim, Germany, 1993). Chromosomal DNA from a potential integrant was isolated using the method described by Eikmanns et al. (Microbiology 140: 1817–1828 (1994)) and each was restricted with the restriction enzymes SacI, PstI and HindIII. The fragments produced were separated using agarose gel electrophoresis and were hybridized at 68° C. with the Dig hybridization kit from Boehringer. Plasmid pCR2.1chrSint mentioned in example 3 had inserted within the chromosomal chrS gene in the chromosome of DSM5715. The strain was called DSM5715:: pCR2.1chrSint.

EXAMPLE 5
Preparing Lysine

The *C. glutamicum* strain DSM5715:: pCR2.1chrSint obtained in example 4 was cultivated in a nutrient medium suitable for the production of lysine and the lysine concentration in the culture supernatant liquid was determined.

For this purpose, the strain was first incubated for 24 hours at 33° C. on agar plates with the corresponding antibiotic (brain-heart agar with kanamycin (25 mg/l). Starting with these agar plate cultures, a preculture was inoculated (10 ml of medium in 100 ml conical flasks). The complete medium CgIII was used as the medium for the preculture.

| Medium Cg III | |
|---|---|
| NaCl | 2.5 g/l |
| Bacto peptone | 10 g/l |
| Bacto yeast extract | 10 g/l |
| Glucose (autoclaved separately) | 2% (w/v) |

The pH was adjusted to pH 7.4

Kanamycin (25 mg/l) was added to this. The preculture was incubated on the shaker at 33° C. for 16 hours at 240 rpm. A main culture was inoculated with this preculture so that the initial OD (660 nm) of the main culture was 0.1 OD. The medium MM was used for the main culture.

| Medium MM | |
|---|---|
| CSL (Corn Steep Liquor) | 5 g/l |
| MOPS | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (filtered sterile) | 0.3 mg/l |
| Thiamine * HCl (filtered sterile) | 0.2 mg/l |
| Leucine (filtered sterile) | 0.1 g/l |
| $CaCO_3$ | 25 g/l |

CSL, MOPS and the salt solution are adjusted to pH 7 with ammoniacal liquor and autoclaved. Then the sterile substrate solution and vitamin solution, and also the dry-autoclaved $CaCO_3$ are added.

Cultivation takes place in 10 ml volumes in a 100 ml conical flask with baffles. Kanamycin (25 mg/l) was added. Cultivation took place at 33° C. and 80% atmospheric humidity.

After 72 hours, the OD was determined at a test wavelength of 660 nm using the Biomek 1000 (Beckmann Instruments GmbH, Munich). The amount of lysine produced was determined with an amino acid analyzer from Eppendorf-BioTronik (Hamburg, Germany) by ion exchange chromatography and post-column derivation with ninhydrin detection.

Table 1 gives the results of the trial.

TABLE 1

| Strain | OD (660 nm) | Lysine-HCl g/l |
|---|---|---|
| DSM5715 | 8.2 | 13.74 |
| DSM5715::pCR2.1chrSint | 9.2 | 14.24 |

The abbreviations and names used are defined as follows:

| | |
|---|---|
| KmR: | Kanamycin resistance gene |
| EcoRI: | Restriction site of restriction enzyme EcoRI |
| HindIII: | Restriction site of restriction enzyme HindIII |
| PstI: | Restriction site of restriction enzyme PstI |
| SacI: | Restriction site of restriction enzyme SacI |
| chrSint: | Internal fragment of the chrS gene |
| ColE1: | Replication origin of the plasmid ColE1 |

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide, which encodes a protein comprising the amino acid sequence of SEQ ID NO:2.

2. The isolated polynucleotide of claim 1, wherein said protein has histidine kinase activity.

3. A vector comprising the isolated polynucleotide of claim 1.

4. A host cell comprising the isolated polynucleotide of claim 1.

5. The host cell of claim 4, which is a Corynebacterium or Escherichia coli.

6. The host cell of claim 4, wherein said host cell is selected from the group consisting of Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum, and Brevibacterium divaricatum.

7. "A method for making a ChrS protein which has histidine kinase activity, comprising culturing the host cell of claim 4 for a time and under conditions suitable for expression of the ChrS protein; and collecting the ChrS protein."

8. An isolated polynucleotide, which comprises SEQ ID NO:1.

9. An isolated polynucleotide, which is complementary to the polynucleotide of claim 8.

10. An isolated polynucleotide, which is at least 90% identical to the polynucleotide of claim 8, and encodes a protein which has ChrS histidine kinase activity.

11. "An isolated polynucleotide which hybridizes under stringent conditions to the polynucleotide of claim 8 or the complement thereof and encodes a protein which has ChrS histidine kinase activity; wherein said stringent conditions comprise washing in 0.5×SSC at a temperature of 68° C."

12. The isolated polynucleotide of claim 8, which encodes a protein having histidine kinase activity.

13. A vector comprising the isolated polynucleotide of claim 8.

14. A host cell comprising the isolated polynucleotide of claim 8.

15. The host cell of claim 14, which is a Corynebacterium.

16. The host cell of claim 14, wherein said host cell is selected from the group consisting of Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum, and Brevibacterium divaricatum.

17. "A method for making a ChrS protein which his histidine kinase activity, comprising
   a) culturing the host cell of claim 14 under conditions suitable for expression of the ChrS protein; and
   b) collecting the ChrS protein."

18. Escherichia coli DSM13982.

19. An isolated polypeptide comprising the amino acid sequence of SEQ ID NO:2.

20. "A process for producing L-amino acids comprising culturing a bacterial cell, in which the chrs gene is not expressed, in a medium suitable for producing L-amino acids, wherein said chrs gene comprises the polynucleotide sequence of SEQ ID NO: 1; and collecting the L-amino acids."

21. The process of claim 20, wherein said bacterial cell is a Corynebacterium or Brevibacterium.

22. The process of claim 20, wherein the bacterial cell is selected from the group consisting of Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum, and Brevibacterium divaricatum.

23. The process of claim 20, wherein said L-amino acid is L-lysine.

24. The process of claim 20, wherein said bacterial cell further comprises at least one gene whose expression is enhanced, wherein said gene is selected from the group consisting of dapA, gap, tp1, pgk, zwf pyc, mqu, lysC, lysE, hom, ilvA, ilvBN, ilvD and zwa 1.

25. The process of claim 20, wherein said bacterial cell further comprises at least one gene whose expression is attenuated, wherein said gene is selected from the group consisting of pck, pgi, poxB, and zwa2.

26. An isolated polynucleotide, comprising nucleotides 302 to 1558 of SEQ ID NO:1.

* * * * *